US00PP35591P2

(12) United States Plant Patent
Bean et al.

(10) Patent No.: US PP35,591 P2
(45) Date of Patent: Jan. 16, 2024

(54) ***AGAPANTHUS* PLANT NAMED 'DWAGHYB02'**

(50) Latin Name: ***Agapanthus* hybrid**
Varietal Denomination: DWAgHyb02

(71) Applicant: De Wet Plant Breeders, Johannesburg (ZA)

(72) Inventors: Quinton Bean, Northriding (ZA); Charles Andrew De Wet, Sandton (ZA)

(73) Assignee: DE WET PLANT BREEDERS, Johannesburg (ZA)

( * ) Notice: Subject to any disclaimer, the term of this patent is extended or adjusted under 35 U.S.C. 154(b) by 0 days.

(21) Appl. No.: 18/112,907

(22) Filed: Feb. 22, 2023

(30) Foreign Application Priority Data

Dec. 7, 2022 (QZ) ..... PBR 20222869

(51) Int. Cl.
*A01H 5/02* (2018.01)
*A01H 6/04* (2018.01)

(52) U.S. Cl.
USPC ..... Plt./398

(58) Field of Classification Search
USPC ..... Plt./398
CPC ..... A01H 5/02; A01H 5/00; A01H 6/04
See application file for complete search history.

(56) References Cited

PUBLICATIONS

Plantipp *Agapanthus* Everpanthus Midnight Sky, retrieved on Jun. 7, 2023 at https://plantipp.eu/uk/varieties/agapanthus-everpanthus-midnight-sky-dwaghyb01pbr, 2 pp. (Year: 2023).*

* cited by examiner

*Primary Examiner* — June Hwu
(74) *Attorney, Agent, or Firm* — Penny J. Aguirre

(57) ABSTRACT

A new cultivar of *Agapanthus* plant named 'DWAgHyb02' that is characterized by its good resistance to root and crown rot, its dense umbels of flowers that are dark purple in color opening from nearly black flower buds, its longer flowering period with light re-blooming, its fast growth habit, its medium height, and its high flower count per umbel.

2 Drawing Sheets

Botanical classification: *Agapanthus* hybrid.
Varietal denomination: 'DWAgHyb02'.

CROSS REFERENCE TO RELATED APPLICATIONS

This application claims priority to European Community Plant Variety Office (CPVO) Plant Breeder's Rights Application No. 2022/2869, filed Dec. 7, 2022. The Applicant received the information for the Plant breeders' rights application directly from the Inventor. This application is co-pending with a U.S. Plant Patent Application filed for a plant derived from the same breeding program that is entitled *Agapanthus* Plant Named 'DWAgHyb01' (U.S. Plant patent application Ser. No. 18/112,983).

BACKGROUND OF THE INVENTION

The present invention relates to a new and distinct cultivar of *Agapanthus* of hybrid origin and will be referred to hereafter by its cultivar name, 'DWAgHyb02'. 'DWAgHyb02' represents a new perennial grown for landscape and container use.

The new cultivar was derived from a controlled breeding program by the Inventors in Hartebeespoort, Northwest Province, South Africa. The goal of the breeding program was to develop a new a cultivar of *Agapanthus* that re-blooms, has dark purple flowers, and is resistant to rot caused by *Erwinia* sp. The Inventors made a cross in October of 2015 between unnamed proprietary plants of

*Agapanthus* from the Inventors' breeding program as both the female and male parents. The Inventors selected 'DWAgHyb02' in October of 2017 as a single unique plant amongst the seedlings that resulted from the above cross.

Asexual propagation of the new cultivar was first accomplished by division by one of the Inventors in Hartebeespoort, Northwest Province, South Africa in October of 2017. Asexual propagation by division and tissue culture utilizing meristematic tissue has determined that the characteristics of the new cultivar are stable and are reproduced true to type in successive generations.

SUMMARY OF THE INVENTION

The following traits have been repeatedly observed and represent the characteristics of the new cultivar. The characteristics in combination distinguish 'DWAgHyb02' as a distinct cultivar of *Agapanthus*.

1. 'DWAgHyb02' exhibits good resistance to root and crown rot.
2. 'DWAgHyb02' exhibits dense umbels of flowers that are dark purple in color opening from nearly black flower buds.
3. 'DWAgHyb02' exhibits a longer flowering period with light re-blooming.
4. 'DWAgHyb02' exhibits a fast growth habit.
5. 'DWAgHyb02' exhibits a medium height.
6. 'DWAgHyb02' exhibits a high flower count per umbel.

The female parent of 'DWAgHyb02' differs from 'DWAgHyb02' in having flowers that are lighter in color. The male parent of 'DWAgHyb02' differs from 'DWAgHyb02' in having flowers that are lighter in color and a slower growth habit. 'DWAgHyb02' can be most closely compared to the *Agapanthus* cultivars 'Black Magic' (not patented), 'DWAgHyb01', and 'Black Pantha' (not patented). 'Black Magic', 'DWAgHyb01', and 'Black Pantha' are all similar to 'DWAgHyb02' in having flowers that are dark in color. 'Black Magic' differs from 'DWAgHyb02' in having flowers that are slightly darker in color and a deciduous habit growth habit and in lacking a re-blooming habit. 'DWAgHyb01' differs from 'DWAgHyb02' in having flowers that are blue in color, a slightly less compact plant habit, a less vigorous growth habit, and less re-blooming. 'Black Pantha' differs from 'DWAgHyb02' in having flowers that are less intense in color, a less vigorous growth habit, and in a better re-blooming habit.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Planttipp, RHS Plants, Cowellsgc, Peter Planttipp (YouTube), Plantestate, Peter van Rijssen (linkedin), Fairweather's Nursery, CND Nursery, Globe Planter, and Crocus.

BRIEF DESCRIPTION OF THE DRAWINGS

The accompanying color photographs illustrate the overall appearance and distinct characteristics of the new *Agapanthus*. The photographs were taken of plants about 2 years in age of 'DWAgHyb02' as grown outdoors in a 30-cm container in Linbro Park, Johannesburg, South Africa.

The photograph in FIG. 1 provides a side view of a plant of 'DWAgHyb02' in bloom.

Figure 1:
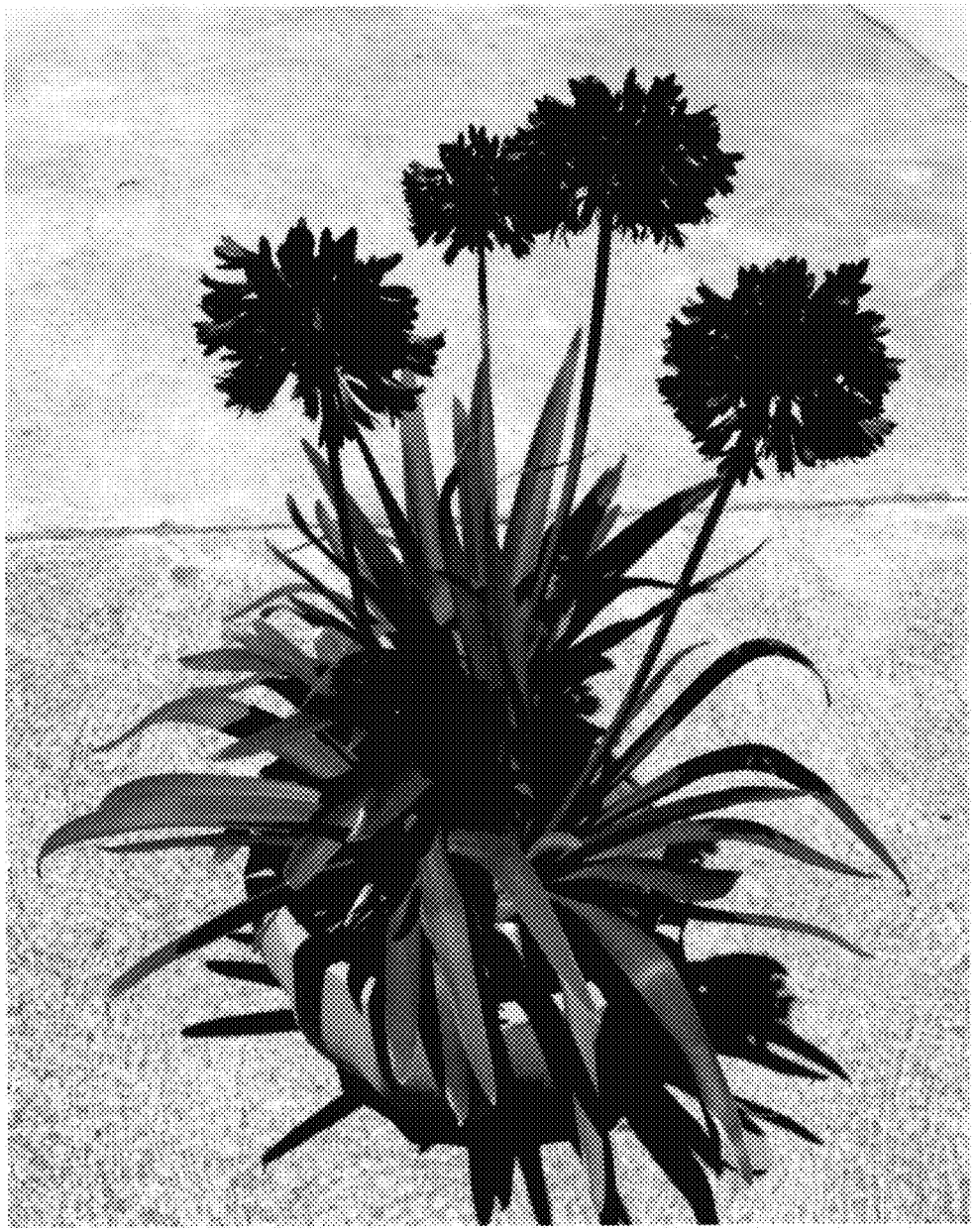
Figure 2:
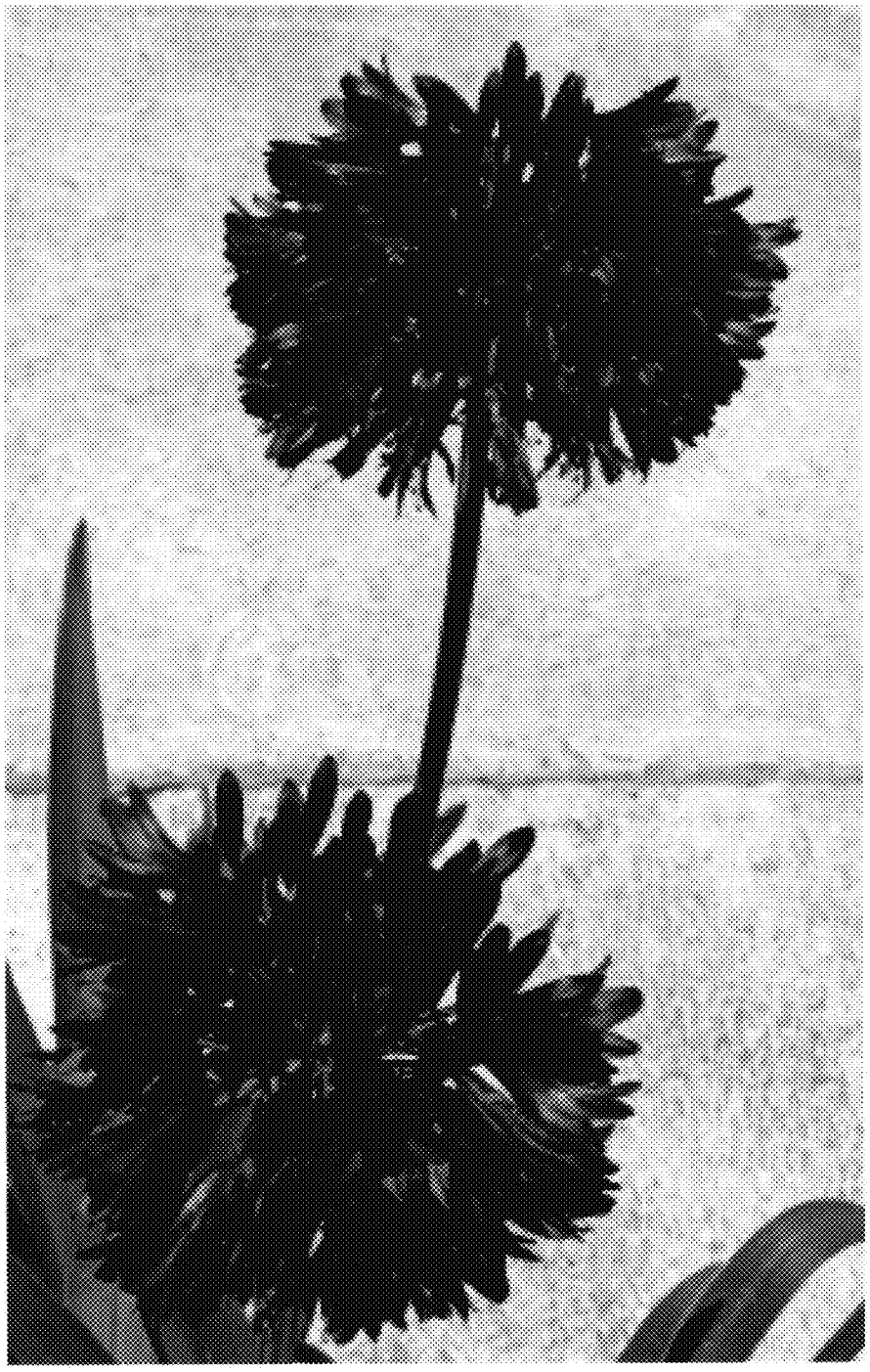

The photograph in FIG. 2 provides a close-up view of an inflorescence of 'DWAgHyb02'.

The colors in the photographs are as close as possible with the photographic and printing technology utilized and color values cited in the detailed botanical description accurately describe the colors of the new *Agapanthus*.

DETAILED BOTANICAL DESCRIPTION

The following is a detailed description of 2-year-old plants of 'DWAgHyb02' as grown outdoors in 17-cm containers in Beaulieu, The United Kingdom. The phenotype of the new cultivar may vary with variations in environmental, climatic, and cultural conditions, as it has not been tested under all possible environmental conditions. The color determinations are in accordance with The 2015 Colour Chart of The Royal Horticultural Society, London, England, except where general color terms of ordinary dictionary significance are used.

General description:

*Blooming period*.—Main bloom early to mid-summer in South Africa, sporadically re-blooming the rest of the year.

*Plant type*.—Herbaceous perennial, evergreen in South Africa however, it is most likely to be semi-evergreen in colder climates (has not been tested).

*Plant habit*.—Compact, basal rosettes with inflorescences emerging from the rosette center.

*Height and spread*.—65 cm in height, 60 cm in width as a 2-year-old plant.

*Cold hardiness*.—At least to U.S.D.A. Zone 8.

*Diseases and pests*.—Good resistance has been observed to crown rot caused by *Fusarium* sp. and root rot caused by *Erwinia* sp., no resistance or susceptibility to pests has been observed.

*Root description*.—Thick and fleshy, 161C in color.

*Propagation*.—Tissue culture (preferred) and division.

*Growth rate*.—Vigorous.

*Number of shoots (rosettes)*.—An average of 4 as grown in a 17-cm container.

Foliage description:

*Leaf shape*.—Ligulate.

*Leaf division*.—Simple.

*Leaf base*.—Truncate.

*Leaf arrangement*.—2-ranked, arranged in shoots an average of 3.5 cm diameter at base.

*Leaf apex*.—Narrow acute.

*Leaf aspect*.—Emerging leaves erect, then cascade.

*Leaf venation*.—Parallel, upper surface; 144A and 144B, lower surface; 137A.

*Leaf margins*.—Entire.

*Leaf size*.—Up to 41 cm in length and up to 2.9 cm in width.

*Leaf surface*.—Smooth, glabrous, and dull on upper and lower surface.

*Leaf number*.—Average of 8 leaves per rosette.

*Foliage density*.—Sparse to medium.

*Leaf color*.—Young leaves upper surface; 144B, base and center more towards the top 138A, young leaves lower surface; 144B, mature leaves upper surface; 137A and 137B (no anthocyanin present), mature leaves lower surface; 137B, base anthocyanin present N92A and 86A in color.

*Leaf attachment*.—Sessile to base.

Flower description:

*Inflorescence type*.—Dense umbel.

*Flower fragrance*.—None.

*Flower type*.—Rotate, campanulate, base of tepals fused.

*Flower number*.—An average of 50 to 60 flowers per umbel.

*Inflorescence size*.—Average of 10 cm in height, 13 cm in diameter.

*Flower size*.—An average of 4 cm in depth and diameter.

*Lastingness of inflorescence*.—Average 7 days.

*Flower aspect*.—Upward to downward.

*Peduncle*.—Very strong, oval in shape, held primarily upright, average of 56 cm in length and 1.5 cm in width, glabrous and slightly glaucous surface, satiny, color; young 144B, mature 137A to 137B, no anthocyanin present.

*Pedicels*.—Very strong, oval in shape, aspect held erect to outward, average of 4.1 cm in length and 1.2 cm in width, glabrous surface, color; 144C.

*Flower buds*.—Obelliptic in shape, average of 4 cm in length and 2.5 cm in width, 79A in color, ovate to lanceolate in shape, acuminate apex, truncate base, up to 4.5 cm in length and 3.5 cm in width, bracts; up to 4.5 cm in length and 3.5 cm in width, color; 144C, base 144B, surface glabrous and dull.

*Tepals* (*perianth*).—6, oblanceolate in shape, lower 25% fused, entire to slightly undulate margins, apex is rounded to acute, glabrous and satiny on inner and outer surfaces, thick substance, an average of 4.1 cm in length and 1.2 cm in width, color; upper surface; 79B to 79C, lower surface 79B to 79C with 79A in the center.

*Bracts*.—Present on one side, ovate to lanceolate in shape, acuminate apex, truncate base, glabrous and matte surface, up to 4.5 cm in length and 3.5 cm in width, color; 144C, veins N77B, base 144B.

Reproductive organs:

*Gynoecium*.—1 pistil, average of 2.3 cm in length, stigma is narrow clavate in shape and 79B in color, style is 2.1 cm in length, color; 79B, base 79C, ovary is oblong in shape, 8 mm in length, 4 mm in width and 145C in color, pistillodes not present.

*Androecium*.—6 stamens, anthers are dorsifixed, extrusion absent to weak, obcordate in shape, average of 2.2 cm in length, and 202A in color, filament is 2.5 cm in length, N155A at base, middle and top 79C to 79D, pollen is abundant and 135B in color, staminodes not present.

*Fruit/seed*.—Have not been observed to date.

It is claimed:

1. A new and distinct cultivar of *Agapanthus* plant named 'DWAgHyb02' as herein illustrated and described.

* * * * *